(12) United States Patent
Al-Aiderous (10) Patent No.: US 11,873,274 B2
(45) Date of Patent: Jan. 16, 2024

(54) NATURAL GAS DEHYDRATION

(71) Applicant: Saudi Arabian Oil Company, Dhahran (SA)

(72) Inventor: Abdullah Y. Al-Aiderous, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 33 days.

(21) Appl. No.: 17/202,044

(22) Filed: Mar. 15, 2021

(65) Prior Publication Data

US 2022/0289653 A1    Sep. 15, 2022

(51) Int. Cl.
*C07C 41/42* (2006.01)

(52) U.S. Cl.
CPC .................... *C07C 41/42* (2013.01)

(58) Field of Classification Search
CPC ...................................... C07C 41/42
See application file for complete search history.

(56) References Cited

U.S. PATENT DOCUMENTS

| | | | |
|---|---|---|---|
| 5,221,523 A * | 6/1993 | Miles | B01D 53/1425 431/5 |
| 5,665,144 A | 9/1997 | Hill et al. | |
| 6,964,729 B1 * | 11/2005 | Khosrowyar | B01D 3/143 95/239 |
| 7,905,722 B1 * | 3/2011 | Heath | B01D 53/002 236/11 |
| 8,876,954 B2 | 11/2014 | Witherspoon et al. | |
| 2011/0247489 A1 | 10/2011 | Witherspoon | |

FOREIGN PATENT DOCUMENTS

CN    102937299 B    12/2014

OTHER PUBLICATIONS

"Fire Tube Reboiler," Product Sheet 8-10-241, Brochure, Heatec, Inc., 2010, 2 pages.
Hicks et al., "Stripburn Simple and Efficient BTEX Control for Direct Fired TEG Reboilers," Proceedings, Annual Convention, Gas Processors Association, Jan. 2007, 2:881-898, 18 pages.

* cited by examiner

*Primary Examiner* — Rosalynd A Keys
(74) *Attorney, Agent, or Firm* — Fish & Richardson P.C.

(57) ABSTRACT

A system and method of regenerating triethylene glycol (TEG) in natural gas dehydration, including removing water from TEG in a TEG regeneration still column having a fired-heater reboiler that includes a burner and a reboiler vessel. The TEG bath temperature in the reboiler vessel and the oxygen gas content in a stack effluent from the burner are controlled automatically via a control system adjusting flow of air and fuel to the burner while maintaining a specified weight ratio of the air to the fuel.

18 Claims, 5 Drawing Sheets

NATURAL GAS DEHYDRATION

TECHNICAL FIELD

This disclosure relates to natural gas dehydration including configuration and operation of a glycol regeneration fired-heater reboiler.

BACKGROUND

Raw natural gas may be generally fully saturated with water vapor when produced from a subterranean formation (underground reservoir). Therefore, raw natural gas is typically subjected to dehydration to remove water to give natural gas for further treatment and commercial distribution. The dehydration of the natural gas (removal of water from the natural gas) may be performed in a process that utilizes glycol (e.g., triethylene glycol) as liquid desiccant.

Carbon dioxide is the primary greenhouse gas emitted through human activities. Carbon dioxide ($CO_2$) may be generated in various industrial and chemical plant facilities. At such facilities, the reduction of generation of $CO_2$ may reduce $CO_2$ emissions at the facility and therefore decrease the $CO_2$ footprint of the facility.

SUMMARY

An aspect relates to a method of regenerating triethylene glycol (TEG) in a natural-gas dehydration system, including removing water from TEG in a TEG regeneration still column having a fired-heater reboiler. The fired-heater reboiler includes a burner and a reboiler vessel. The method includes controlling TEG bath temperature in the reboiler vessel and weight percent of oxygen gas in stack effluent from the burner by a control system automatically adjusting flow of air and fuel to the burner while maintaining a specified ratio of the air to the fuel.

Another aspect relates to a method of regenerating TEG in a natural-gas dehydration system, including feeding rich TEG to a TEG regeneration still column having a fired-heater reboiler that includes a burner and a reboiler vessel. The rich TEG is TEG rich in water. The method includes feeding air and fuel to the burner at a specified ratio of the air to the fuel, and controlling TEG bath temperature in the reboiler vessel per a set point automatically via a control system. The method includes controlling weight percent of oxygen gas in a stack effluent from the burner in a specified weight-percent range automatically via a control system, wherein controlling the TEG bath temperature and controlling the weight percent of oxygen gas in the stack effluent comprise the control system automatically adjusting flow of the air and the fuel to the burner at the specified ratio. The method includes removing water from the rich TEG in the TEG regeneration still column.

Yet another aspect relates to natural-gas dehydration system including a TEG regeneration still column to receive rich TEG, discharge water vapor overhead, and discharge lean TEG from a reboiler vessel for feed to a contactor column. The TEG regeneration still column has a fired-heater reboiler including a burner and the reboiler vessel. The natural-gas dehydration system includes an air control valve to control flow rate of air to the burner and a fuel control valve to control flow rate of fuel to the burner. The natural-gas dehydration system includes a control system to adjust automatically an air set point of the air control valve and a fuel set point of the fuel control valve to control TEG bath temperature in the reboiler vessel, control weight percent of oxygen gas in stack effluent from the burner, and maintain a ratio of the air to the fuel at a specified ratio. The natural-gas dehydration system includes a temperature sensor at the reboiler vessel to measure the TEG bath temperature, and a temperature transmitter to indicate the TEG bath temperature as measured by the temperature sensor to the control system.

The details of one or more implementations are set forth in the accompanying drawings and the description below. Other features and advantages will be apparent from the description and drawings, and from the claims.

DETAILED DESCRIPTION

Some aspects of the present disclosure are directed to a natural-gas dehydration system having a natural-gas dehydration subsystem and a triethylene glycol (TEG) regeneration subsystem. The natural-gas dehydration subsystem may labeled as a TEG dehydration subsystem in that natural-gas dehydration subsystem utilizes TEG to dehydrate the natural gas.

The overall natural-gas dehydration system may have: (1) a contactor column (absorber) to dehydrate the natural gas with TEG as liquid desiccant; and (2) a TEG regeneration column (still) to remove water from the TEG. The rich TEG from the contactor column may enter the TEG regeneration column. In the TEG reboiler of the TEG regeneration system, the TEG is boiled via a heating element, which may involve a fired heater to heat the TEG to the water vaporization temperature to vaporize the water that was absorbed in the contactor column. The TEG reboiler is associated with the TEG regeneration column.

The fired heater may utilize natural gas as fuel and may have an exhaust stack. The rich TEG as boiled in the reboiler may thus be converted to lean TEG (e.g., at a purity of 99%) and sent back to the contactor column for the natural gas dehydration. TEG regeneration fired-heaters may typically include a burner that combusts a mixture of air and fuel (e.g., natural gas) to release heat via the firing process to the TEG bath in the reboiler vessel to achieve the desired TEG bath temperature.

The present disclosure is directed to automated control of TEG bath temperature in a fired-heater reboiler of the TEG regeneration column (still) in a natural-gas dehydration system that utilizes the TEG as liquid desiccant in a contactor column (absorber column) to dehydrate natural gas. A control system adjusts, via control valves, the rates of fuel (e.g., natural gas) and air fed to the fired-heater reboiler burner to give the fired-heater combustion duty for the specified bath temperature in the reboiler vessel and according to a specified weight ratio (or volume ratio) of fuel to air.

The oxygen gas content in the stack effluent from the burner may be controlled as a secondary variable to below a specified maximum (and above a specified minimum).

Aspects may give increase efficiency of fired-heater combustion to meet fired-heater bath temperature with optimized or beneficial utilization of fuel (e.g., natural gas) and reduced amount of incomplete-combusted effluent gas. The techniques may integrate control between feed of air and fuel gas with an oxygen analyzer on the reboiler exhaust stack. Embodiments may include automatically adjusting the flow rates of air and fuel in reference to the oxygen analyzer and specified bath temperature while maintaining an air-to-fuel ratio. Such automation may avoid inefficient combustion. Certain implementations may reduce lower overall fuel (natural gas) consumption, lower incomplete combustion products, and result in less thermal energy losses. Aspects can include techniques to achieve the desired bath temperature of a fired-heater reboiler in a TEG regeneration system in an automated fashion that may optimize or give beneficial fuel gas consumption, increased combustion efficiency, reduced TEG losses, and increased equipment lifetime.

The desired temperature in the TEG regenerator reboiler bath may be, for example, in the range of 390° F. to 395° F. to remove absorbed water from the TEG that was absorbed in the natural gas dehydration. The TEG bath temperature range may be specified to achieve the desired TEG purity, e.g., 99 weight percent (wt %), through the vaporization of water that was absorbed into the TEG in the natural gas dehydration that utilized the TEG. Moreover, TEG degrades at a temperature of 404° F. resulting in a relatively small operating margin between water vaporization temperature and the TEG degradation temperature. In order to achieve the desired bath temperature in the fired-heater reboiler, fuel (e.g., natural gas) and air are mixed and combusted in the fired-heater burner at specified flow and specified (determined or calculated) ratio to achieve the heat duty.

As mentioned, the natural-gas dehydration system may include at least two subsystems: the natural-gas dehydration subsystem (employing TEG) and the TEG regeneration subsystem. In the natural-gas dehydration subsystem, lean TEG is pumped to the contactor column (an absorption column). The lean TEG dehydrates the natural gas (hydrocarbon gas) in the contactor column due to the TEG affinity for water, which as a result, turns the lean TEG to rich TEG. The TEG regeneration system converts the rich TEG from the contactor column to lean TEG by removing the absorbed water by heating the TEG solution and boiling off the water.

Fuel and air are introduced to the fire-heater reboiler burner of the TEG regeneration system through control valves that control flow rates of both streams. The control valves may be pressure control valves or flow control valves. Both the air and the fuel are mixed at a specified or calculated ratio (e.g., air-to-fuel=10:1) and combusted via the fired-heater combustion to heat the reboiler vessel internally and the TEG bath. The TEG bath temperature is elevated to reach the desired temperature range (e.g., 390° F. to 395° F.) and is maintained at the desired temperature. The air-to-fuel ratio may be set to an efficient ratio based on industry standards or based on calculation and quality (composition) analysis of fuel samples. The control system may send a command to adjust flow rates the fuel and air to achieve the fired-heater combustion duty and bath temperature by modulating the control valves to increase or decrease flow while maintaining the preset air-to-fuel ratio. The bath temperature achieved may be verified by the control system via the bath temperature transmitter.

An oxygen analyzer on the stack effluent from the burner may send readings to the control system. The control system may send a command to adjust flow rates of fuel and air to the burner to meet a specification(s) for the oxygen gas content in the boiler stack effluent as measured by the oxygen analyzer. The specification may include a maximum value (e.g., 3 wt % or 4 wt %) and a minimum value (e.g., 1 wt % or 2 wt %). To lower the oxygen-gas weight percent to the minimum value, the control system may send a command to the fuel and air control valves to reduce flow rates to reduce effluent oxygen readings to the lower limit of while maintaining the desired TEG bath temperature.

In order for the control system parameters not to compete for control, the desired bath temperature set point may be maintained as the main governing parameter with system components adjusting to achieve the temperature parameter, then secondarily adjusting to satisfy the effluent oxygen-gas specification, and optimizing the natural-gas consumption rate.

Lastly, while the discussion herein may focus on TEG, it should be understood that TEG is one example of glycol that may be employed as the liquid desiccant in a natural-gas dehydration system. Other glycols may be employed as the liquid desiccant in the present techniques. Other examples include diethylene glycol (DEG), ethylene glycol (MEG), and tetraethylene glycol (TREG). TEG is the most commonly used glycol in industry for natural gas dehydration. Indeed, the generic term "glycol" may be implicitly considered as TEG in some instances of natural gas dehydration.

Figure 1:
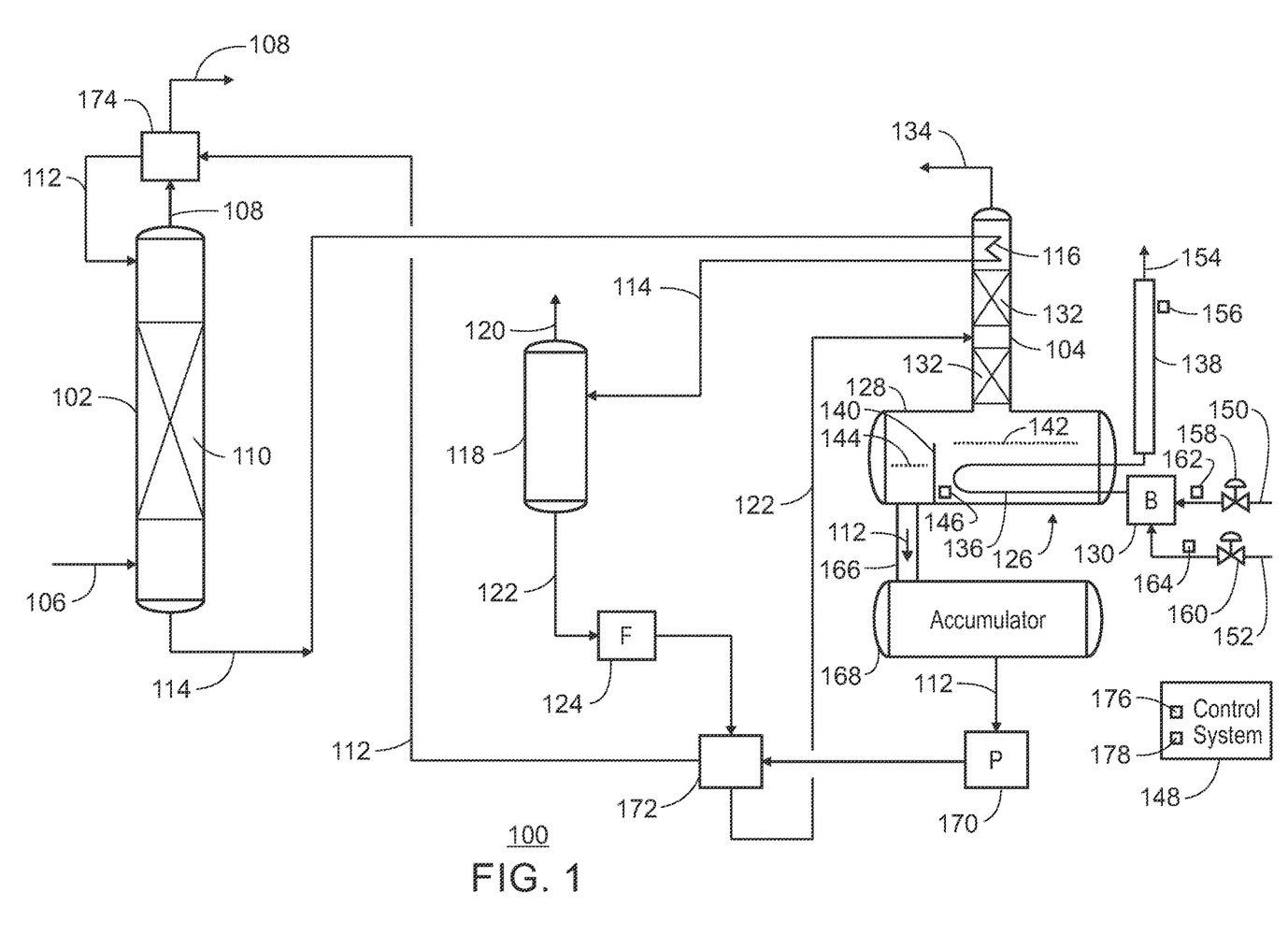
FIG. 1 is a diagram of a natural-gas dehydration system that includes a contactor column and a TEG regeneration still column.

FIG. 1 is a natural-gas dehydration system 100 that includes a contactor column 102 and a TEG regeneration still column 104. The equipment and processing between the contactor column 102 and TEG regeneration still column 104 as depicted in the illustrated embodiment of FIG. 1 are given as an example. Other configurations are applicable, such as with respect to the handling and processing of the rich TEG and lean TEG between the two columns 102, 104.

In operation, the contactor column 102 receives wet natural gas 106 and contacts the natural gas 106 with TEG as liquid desiccant for the TEG to absorb water from the natural gas 106. The TEG regeneration system regenerates (removes water from) the TEG to give dried (lean) TEG for re-use as the absorbing TEG in the contactor column 102.

The contactor column 102 is a vessel that is an absorption column. The contactor column 102 employs the TEG to remove (absorb) water from the natural gas 106 to give the dehydrated (dried) natural gas 108. The contactor column 102 may also be called a contactor tower, absorber, absorber column, absorption column, dehydrator, dehydrator column, glycol contactor, glycol contactor column, TEG contactor column, and so forth. The contactor column 102 utilizes the TEG to dehydrate the natural gas 106 to give dehydrated natural gas 108 as product for distribution or further processing.

As denoted by reference numeral 110, the contactor column 102 may include column trays (e.g., bubble cap traps, sieve trays, etc.) or packing (e.g., random packing or structured packing) to provide mass-transfer stages and surface area for absorption of water by the TEG from the natural gas. In the case of bubble cap trays, the natural gas flowing upward through the bubble caps may form small bubbles providing surface area for mass transfer of water from the natural gas into the TEG. In the case of packing, the liquid TEG flowing downward may form as a thin film on the packing providing surface area for the mass transfer of water from the natural gas into the TEG.

The contactor column 102 may receive the wet natural gas 106 into a lower portion of the contactor column 102. The contactor column 102 may have an inlet nozzle coupled (e.g., flanged, threaded, etc.) to an inlet conduit conveying the natural gas 106 to the contactor column 102. The natural gas 106 entering the contactor column 102 may flow upward through the contactor column 102.

In implementations, the natural-gas dehydration system 100 may include an inlet separator (not shown) that removes condensed or entrained liquid from the wet natural gas 108 before water is removed the natural gas 108 via the TEG. The inlet separator can be a separation vessel disposed upstream of the contactor column 102 or built into a bottom portion of the contactor column 102. The inlet separator may operate to knock out liquid entrained in the wet natural gas 108. For example, the inlet separator may have a mist eliminator section in a top portion of the inlet separator vessel. In operation, small liquid droplets in the gas 108 may coalesce on fine wire mesh of the mist eliminator and form larger liquid droplets that move into a liquid section in a lower portion of the inlet separator vessel. The inlet separator may equipped with liquid level controls for the accumulated liquids to discharge from a bottom portion of the inlet separator vessel through a level control valve.

The contactor column 102 may receive lean TEG 112 into an upper portion of the contactor column 102. The term "lean" means that the TEG is lean in water and may have less than 1 wt % water. The contactor column 102 may receive lean TEG 112 from the TEG regeneration still column 104. The contactor column 102 may have an inlet nozzle coupled (e.g., flanged, threaded, etc.) to an inlet conduit conveying the lean TEG 112 to the contactor column 102. The lean TEG 112 entering the contactor column 102 may flow downward through the contactor column 102. Thus, the natural gas and TEG may be in a counter current flow with respect to each other in the contactor column 102 for the absorption of water from the natural gas into the TEG.

The dehydrated natural gas 108 may discharge overhead from the contactor column 102 through a discharge conduit. The contactor column 102 may have an outlet nozzle on the top or top portion of the contactor column 102. The outlet nozzle may be coupled (e.g., flange connection, screwed or threaded connection, etc.) to the overhead discharge conduit. In implementations, the dehydrated natural gas 108 may have a concentration of water less than 7 pounds per million standard cubic feet.

Rich TEG 114 may discharge through a discharge conduit from a bottom portion of the contactor column 102. The contactor column 102 may have an outlet nozzle on the bottom portion of the contactor column 102 that is coupled (e.g., flange connection, screwed or threaded connection, etc.) to a bottoms discharge conduit. The term "rich" means that the TEG is rich in water, such as saturated (or approaching saturation) in water. The rich TEG 114 may have a concentration of water of at least 2 wt %, such as in a range of 2 wt % to 6 wt %.

In implementations, the rich TEG 114 may be routed through a heat exchanger (e.g., piping coils 116) in an upper portion of the TEG regeneration still column 104 to cool water vapor in the upper portion of the TEG regeneration still column 104. Such also preheats the rich TEG 114. In the illustrated embodiment, the rich TEG 114 as heated may flow to a flash vessel 118 (e.g., flash tank, flash drum, separation vessel, etc.).

The flash vessel 118 operates at a pressure lower than the pressure in the contactor column 102. The pressure in the flash vessel 118 may be, for example, in a range of 15 pounds per square inch gauge (psig) to 50 psig. Gases dissolved in the rich TEG 114 evolve from the TEG 114 in the flash vessel 118. Liquid hydrocarbon in the rich TEG 114 may flash (vaporize) in the flash vessel 118. The evolved gases including the flashed hydrocarbons may discharge overhead as flash gas 120 from the flash vessel 118. In some implementations, liquid hydrocarbons may be skimmed from the TEG 114 in the flash vessel 118 (e.g., for instances with the flash vessel 118 as a three-phase separator).

Rich TEG 122 may discharge from a bottom portion of the flash vessel 118. The rich TEG 122 that discharges from the flash vessel 118 may be the rich TEG 114 that enters the flash vessel 118 minus the flash gas 120 (any removed liquid hydrocarbon). The rich TEG 122 may flow through a filter 124 to remove solids (if present) from the rich TEG 122. In examples, the solids removed may be solid particles having a particle size of at least 5 microns. The filter 124 may be a filter vessel housing a filter element. The filter 124 may be, for example, a particulate filter or carbon filter. Solids removed can include impurities and degraded TEG. The removal of solids can avoid, for example, fouling or plugging of packing in the TEG regeneration still column 104 with the solids.

The rich TEG 122 may be provided to a TEG regeneration system. The TEG regeneration system may include the TEG regeneration still column 104 and associated equipment. The TEG regeneration still column 104 may also be called a TEG regeneration still, glycol regeneration still, TEG regenerator, glycol regenerator, and so on. Again, the TEG regeneration still column 104 (and associated equipment or system) may be called a TEG regenerator or TEG regeneration system. The TEG regeneration system removes water from the rich TEG 122 to give the lean TEG 112 for re-use in the contactor column 102. The TEG regeneration still column 104 recovers (condenses) vaporized TEG accompanying the vaporized water flowing upward through the column.

The TEG regeneration still column 104 is a distillation column (vessel) having a fired-heater reboiler 126 that provides heat for the distillation. The fired-heater reboiler 126 includes a reboiler vessel 128 and a burner 130. The fired-heater reboiler 126 may be characterized as a component of the TEG regeneration system or as a component associated with the TEG regeneration still column 104. The performed distillation is to distill (remove) water from the rich TEG 122.

As generally with distillation columns having a reboiler, the reboiler may be a heat exchanger disposed external (and adjacent) to the distillation column vessel but that is associated with and operates in tandem with distillation column vessel. Thus, in stating that a distillation column (e.g., TEG regeneration still column 104) has or comprises a reboiler (e.g., fired-heater reboiler 126), it is understood that the reboiler is typically not inside the column vessel.

The TEG regeneration still column 104 may include one or more sections 132 of packing or distillation trays for the distillation performed by the TEG regeneration still column 104. The section 132 (or each section 132) may be a bed of packing, or a packing bed.

In the illustrated example, the rich TEG 122 as feed enters a middle portion of the column vessel of the TEG regeneration still column 104. The TEG regeneration still column 104 may have a feed nozzle coupled to the inlet conduit transporting the rich TEG 122 to the TEG regeneration still column 104. The feed nozzle may be coupled to the inlet conduit, for example, via flanges (flanged connection) or threads (screwed connection).

In addition, in some examples, the TEG regeneration still column 104 may include a column internal (e.g., distributor, spray nozzle, etc.) to initially apply the rich TEG 122 as received. In one example, the column internal is one or more spray nozzles disposed between the two depicted sections 132 of packing, such that the spray nozzle(s) sprays the rich TEG 122 onto the lower section 132 of packing.

In operation, the water removed from the TEG may discharge overhead as water vapor 134 from a top portion of the TEG regeneration still column 104 into an overhead discharge conduit. An outlet nozzle on a top portion of the TEG regeneration still column 104 may be coupled (e.g., flange connection, screwed or threaded connection, etc.) to the overhead discharge conduit for discharge of the water vapor 134 from the TEG regeneration still column 104.

As for the reboiler, water vapor may flow upward from the reboiler vessel 128 through the column vessel of the TEG regeneration still column 104. In this distillation in the column vessel, mass transfer of water occurs from the rich TEG 122 into the water vapor flowing upward through the column. The column packing 132 (or trays) may facilitate or promote such mass transfer (and heat transfer from the hot water vapor into the cooler rich TEG 122). The vapor flowing upward from the reboiler vessel 128 into the column may be primarily water vapor with trace TEG. The packing 132 may facilitate to capture (condense) the vaporized TEG via condensation of the vaporized TEG for recovery into the lean TEG 112. The piping coils 116 (column internal) at the upper portion of the column may cool the water vapor before discharged as water vapor 134 stream from the TEG regeneration still column 104.

The TEG regeneration still column 104 may additionally be considered as a stripper (e.g., water stripper) and thus labeled as a TEG regeneration system stripping column in cases in which a stripping gas (e.g., natural gas, flash gas 120, etc.) is introduced into the reboiler vessel 128 to flow upward to strip (remove, absorb) water from the TEG. The stripping gas, if employed, may discharge in the water vapor 134. In some implementations, the natural-gas dehydration system 100 may include a separate stripping column (in addition to the TEG regeneration still column 104) to employ stripping gas to strip water from the TEG.

In the illustrated implementation, the TEG regeneration still column 104 includes its column vessel coupled (e.g., via flanges) to the reboiler vessel 128 for fluid flow between the column vessel and the reboiler vessel 128. The flange if employed on the column vessel may be a vessel flange.

The burner 130 may be a direct-fired burner or an indirect-fired burner. In operation, the burner 130 generates heat for the TEG in the reboiler vessel 128. In the illustrated embodiment, a fire tube 136 (heating tube, tubing, conduit, coils, etc.) positioned in the reboiler vessel 128 originates from the burner 130 and discharges into an exhaust stack 138. Employment of the fire tube 136 makes the burner 130 an indirect fired-heater burner. However, the burner 130 can instead be a direct fired-heater burner. The stack 138 may also be called a flue and can generally be a conduit. In some examples, the stack 138 can be a smokestack scrubber.

The TEG in the reboiler vessel 128 may be labeled as a TEG bath of the fired-heater reboiler 126. In certain examples, the reboiler vessel 128 may include a weir 140 to maintain a liquid level 142 of TEG (TEG bath), such as above the fire tube(s) 136. In some examples, the liquid level 142 of TEG is the TEG bath. In operation, the TEG may overflow the weir 140 into a lower liquid level 144 of lean TEG 112 for discharge of the lean TEG 112 from the reboiler vessel 128.

A temperature sensor 146 may be situated in the reboiler vessel 128 to measure TEG bath temperature. The TEG bath temperature is the temperature of the TEG (TEG bath) in the reboiler vessel 128. The temperature sensor 146 may be, for example, a thermocouple or a resistance temperature detector (RTD). If a thermocouple is employed, the thermocouple may be situated in a thermowell inserted into the reboiler vessel 128. The TEG bath temperature as measured by the temperature sensor 146 may be communicated or indicated to a control system 148 (e.g., in real time). In examples, an instrument (temperature) transmitter may communicate or indicate the TEG bath temperature as measures by the temperature sensor 146 to the control system 148.

In operation, the burner 130 provides heat for the TEG bath to drive the distillation. Fuel 150 (e.g., fuel gas) and air 152 may be fed to the burner 130 for combustion of the fuel 150 to provide heat for the TEG (TEG bath) in the reboiler vessel 128. In the depicted example, combustion gases (generated in the combustion) flow from the burner 130 through the fire tube 136 for heat transfer from the combustion gases in the fire tube 136 to the TEG to heat the TEG. The fired-heater reboiler 126 can include, for instance, a refractory-lined impingement plate for the combustion gases from the burner 130. A variety of configurations of the fired-heater reboiler 126 with respect to routing of the combustion gases and heat transfer are applicable. A fired-heater reboiler 126 can include multiple fire tubes 136 and multiple passes of the fire tubes 136. As the hot combustion gases flow through the fire tubes 136 immersed in the TEG bath, the walls of the fire tubes 136 are heated by the combustion gases and the heat transferred into the TEG.

The combustion gases may discharge as stack effluent 154 (flue gas, exhaust gas, stack gas, etc.) through the stack 138. In implementations, the stack effluent 154 may discharge from the stack 138 to the surrounding environment as emissions.

An oxygen analyzer 156 as an online instrument may be disposed along the exhaust stack 138 (or at the discharge of the exhaust stack 138) to measure oxygen gas concentration in the stack effluent 154. The oxygen analyzer 156 or an instrument transmitter may communicate or indicate the oxygen gas concentration as measured by the oxygen analyzer 156 to the control system 148. In implementations, the readings relied on from the oxygen analyzer may be the concentration of oxygen gas that generally does not include elemental oxygen of other compounds in the stack effluent 154. Moreover, it should be understand that when referring to control of the "oxygen" concentration or the amount of "oxygen" in the stack effluent, such is the amount of oxygen gas ($O_2$). The oxygen analyzer 156 may include the instrument transmitter that interfaces and communicates with the control system 148 to indicate the measured oxygen-gas concentration of the stack effluent 154 to the control system 148. The measurement may be measurement of a sample of the stack effluent 154 collected online from the stack 138. The measurement may be an in-situ measurement directly in the flow of the stack effluent 154 in the stack 138. In examples, the oxygen analyzer 156 may include a probe inserted into the stack 138 and an interface external to the stack 138. An example of the oxygen analyzer 156 is the oxygen analyzer system ZR22 available from Yokogawa Electric Corporation having headquarters in Tokyo, Japan. Other on-line oxygen analyzers are applicable.

The oxygen gas concentration in the stack effluent 154 may be relevant as a parameter to indicate combustion efficiency in the burner 130. The combustion efficiency may include the percent complete combustion. Incomplete combustion can waste fuel. The combustion efficiency may be affected by the air-to-fuel ratio. Further, at a constant air-to-fuel ratio, the combustion efficiency may be affected by the combined amount of fuel 150 and air 152 fed to the burner 130. Combustion analysis may be part of a process to improve fuel economy and reduce emissions of greenhouse gases, such as carbon dioxide.

Embodiments herein may provide increased combustion efficiency through control of the fuel 150 and air 152 to the burner 130, including at a constant air-to-fuel ratio. Such may more efficiently utilize the fuel (less waste) and reduce emissions of carbon dioxide. In addition, the improve control and efficiency of the combustion in the burner 130 may advantageously lower the burner 130 temperature more consistently and thus reduce fouling in the burner 120, fire tube 136, stack 138, and therefore reduce maintenance costs and extend equipment life.

The fuel 150 may be fuel gas and may typically be or include natural gas. The natural gas for the fuel 150 may be from a natural-gas supply header in the plant or facility, and/or may be a slipstream from the product natural gas 108 discharged from the contactor column, and the like. Natural gas may be methane, for example, at 70-90 mole percent (mol %). Natural gas may include higher alkanes (e.g., ethane, propane, butane) and other components (e.g., nitrogen, hydrogen, sulfide, etc.) at a combined concentration, for example, less than 30 mol %. In certain embodiments, the natural gas includes at least 80 mol % methane or at least 90 mol % methane. In embodiments, the natural gas may have no measurable oxygen gas and/or no measurable water, or have trace amounts of oxygen gas and/or water. In examples, natural gas generally has no more than 1 mole percent (mol %) of oxygen gas and no more than 1 mol % of water.

A fuel control valve 158 is disposed along the inlet conduit conveying the fuel 150 to the burner 130. A supply header (conduit) may provide the fuel 150 through the inlet conduit. Motive force for flow of the fuel 150 through the fuel control valve 158 to the burner 130 may be the supply header pressure (e.g., natural-gas supply header or sub-header). The fuel control valve 158 may control the flow rate of the fuel 150 to the burner 130. The fuel control valve 158 may be a flow control valve that controls the flow rate of the fuel 150 per a flow-rate set point. The fuel control valve 158 can be a pressure control valve that controls pressure of the fuel 150 fed to the burner 130 to maintain the pressure per a pressure set point. For the fuel control valve 158 as a pressure control valve, the control valve 158 controls the flow rate of the fuel 150 to control the pressure of the fuel 150. The pressure of the fuel 150 fed to the burner 130 may be measured downstream of the control valve 158. The pressure of the fuel 150 as measured may be communicated or indicated to the control system 148 (e.g., in real time).

An air control valve 160 is disposed along the inlet conduit conveying the air 152 to the burner 130. The air control valve 160 may control the flow rate of the air 152 to the burner 130. The air 152 may be, for example, plant air or instrument air at the facility. Thus, the motive force for flow of the air 152 may be the supply header pressure (provided by an upstream mechanical compressor) for the plant air or instrument air. The air 152 may be, for example, ambient air from the surrounding environment. A motive device, such as a fan, may provide motive force for flow of the air 152 through the air control valve 160 to the burner 130.

The air control valve 160 may be a flow control valve that controls the flow rate of the air 152 per a flow-rate set point. The air control valve 160 can be a pressure control valve that controls pressure of the air 152 fed to the burner 130 to maintain the pressure per a pressure set point. For the air control valve 160 as a pressure control valve, the control valve controls the flow rate of the air 152 to control the pressure of the air 152. The pressure of the air 152 fed to the burner 130 may be measured downstream of the air control valve 160. The pressure of the air 152 as measured may be communicated or indicated to a control system 150 (e.g., in real time).

A fuel flow meter 162 may be disposed downstream (as depicted) or upstream of the fuel control valve 158 to measure the flow rate of the fuel 150. An air flow meter 164 may be disposed downstream (as depicted) or upstream of the air control valve 160 to measure the flow rate of the air 152. The meters 162, 164 may be, for example, a Venturi tube meter, an orifice type meter, or an ultrasonic meter. In one example, the fuel flow meter 162 and the air flow meter 164 are each a differential-pressure (DP) flow meter (e.g., having an orifice in-line and pressure taps).

The flow rate of the fuel 150 as measured by the fuel flow meter 162 may be communicated or indicated, e.g., via an instrument (flow) transmitter, to the control system 150 (e.g., in real time). The controller, e.g., flow controller (FC), in the control system 148 for the fuel control valve 158 may modulate the valve opening percent of the control valve 158 in response to the measured flow rate of the fuel 150 to maintain the fuel 150 flow rate (or pressure) per set point of the fuel control valve 158. The flow rate of the air 152 as measured by the air flow meter 164 may be communicated or indicated, e.g., via an instrument (flow) transmitter, to the control system 148 (e.g., in real time). The controller, e.g., flow controller (FC), in the control system 148 for the air control valve 160 may modulate the valve opening percent of the control valve 160 in response to the measured flow rate of the air 152 to maintain the air 152 flow rate (or pressure) per set point of the air control valve 158.

A desired weight (mass) ratio or volume ratio of the air-to-fuel (air 152 to fuel 150) fed to the burner 130 may be programmed or entered (e.g., by a human operator) into the control system as a constraint. Therefore, respective adjustments (by the control system 148) to the flow of air 152 and the flow of fuel 150 to the burner 130 are proportional so to maintain the specified air-to-fuel weight ratio. This may occur, for example, when the control system 148 is controlling TEG bath temperature or the oxygen gas content in the stack effluent 154. An example of a desired or specified air-to-fuel weight ratio is 10. A new air-to-fuel ratio may be calculated and entered, for example, when the quality or composition of the fuel 150 changes. The fuel 150 may be sampled and tested.

The temperature of the TEG in the reboiler vessel 128 (the TEG bath temperature in the reboiler vessel 128) is generally maintained below 404° F., which is the degradation temperature of TEG. A temperature set point for the TEG bath temperature may be entered (e.g., by a human operator) into the control system 148. The temperature set point may be a specific value (e.g., 393° F., 395° F., etc.), such as in ranges of 390° F. to 400° F., or 390° F. to 395° F. To meet the set point, the control system 148 may automatically adjust the fuel 150 and air 152 in response to the measured TEG bath temperature value from the temperature sensor 146 in the reboiler vessel 128 received by the control system 148. The adjustment to the fuel 150 may be proportional to the adjustment to the air 152 to keep the air-to-fuel ratio the same. Thus, increases or decreases to the flow rates of the fuel 150 and air 152 are made in tandem.

To maintain the entered set point of the TEG bath temperature, the control system 148 may adjust (e.g., automatically) the set point of the fuel control valve 158 and the set point of the air control valve 160. The set point of the fuel control valve 158 specified (and adjusted) by the control system 148 may be a flow-rate set point or a pressure set point. Likewise, the set point of the air control valve 160 specified (and adjusted) by the control system 148 may be a flow-rate set point or a pressure set point.

The control system 148 may include a TEG bath temperature controller in a master-slave relationship with the two valve 158, 160 controllers. The TEG bath temperature controller as a master controller may specify and adjust the set point (e.g., flow rate or pressure) of the controller (as slave controller) for the fuel control valve 158, and specify and adjust the set point (e.g., flow rate or pressure) of the controller (as slave controller) for the air control valve 160. In specifying or adjusting the respective set points of the control valves 158, 160 to meet the entered TEG bath temperature set point, the control system 104 may maintain constant the air-to-fuel weight (mass) ratio. Moreover, the control system 148 may also make adjustments to maintain the oxygen gas concentration in the stack effluent 154 in a specified range.

As for the weight percent of oxygen gas in the stack effluent 154 (as measured by the oxygen analyzer 156), desired values of weight percent of oxygen gas may be entered (e.g., by a human operator) into the control system 148. Entered may be a maximum weight percent (e.g., 3 wt % or 4 wt %) of oxygen gas, a minimum weight percent (e.g., 1 wt % or 2 wt %) of oxygen gas, and/or a range of minimum weight percent of oxygen gas to maximum weight percent of oxygen gas. Examples of specified ranges for weight percent of oxygen gas in the stack effluent 154 entered into the control system 148 may include 1 wt % to 4 wt %, 1 wt % to 3 wt %, 2 wt % to 4 wt %, and 2 wt % to 3 wt %.

It may be desired to maintain the weight percent of O2 in the stack effluent 154 below a maximum value so to advance or reflect combustion completion at the burner 130 and to avoid wasting fuel 150. A benefit may be to reduced emissions of greenhouse gases in the stack effluent 154. Higher percentages of O2 may be indicative of higher percentages of carbon dioxide (CO2). It may be desired to maintain the weight percent of O2 in the stack effluent 154 above a minimum value so to promote or reflect that an adequate amount (or beneficial amount) of combustion occurs at the burner 130 for heating the TEG bath.

The weight percent of O2 in the stack effluent 154 may be a secondary variable in comparison to the TEG bath temperature as a primary variable. While the control system 148 may control or maintain the weight percent O2 per a specified minimum, specified maximum, or specified range, the control system 148 may allow the measured weight percent O2 to fail to satisfy the specified values if needed to maintain TEG bath temperature per set point.

To satisfy the specified values for weight percent O2 in the stack effluent 154, the control system 148 may automatically adjust the fuel 150 and air 152 in response to the measured weight percent value from the oxygen analyzer 156. As with TEG bath temperature control, the adjustment to the fuel 150 may be proportional to the adjustment to the air 152 to keep the air-to-fuel ratio the same. Thus, in the control of the weight percent O2 in the stack effluent 154, respective changes to the flow rates of the fuel 150 and air 152 may be made in tandem.

To maintain the weight percent O2 in the stack effluent 154 per the specified values (e.g., maximum value or range) entered into the control system 148, the control system 148 may automatically specify and adjust the set point (e.g., flow rate or pressure) of the fuel control valve 158 and the set point (e.g., flow rate or pressure) of the air control valve 160. The control system 146 may include an O2 weight-percent controller (for the stack-effluent 154) as a component of a master controller having the TEG bath temperature controller. While the O2 weight-percent controller may be a master controller, the priority of the O2 weight-percent controller may be lower than the priority of the TEG bath temperature controller.

The stack-effluent weight-percent O2 controller may be in a master-slave relationship with the two valve 158, 160 controllers. The stack-effluent weight-percent O2 controller as a master controller may specify (and adjust) the set point of the controller (as slave controller) for the fuel control valve 158 and specify (and adjust) the set point of the controller (as slave controller) for the air control valve 160. In specifying or adjusting the respective set points of the control valves 158, 160 to meet the entered weigh percent value or values, the control system 104 may maintain constant the air-to-fuel weight ratio.

Other control configurations are applicable. For instance, the TEG bath temperature controller or the stack-effluent weight-percent O2 controller, or combination thereof, in the control system 148 may adjust (modulate) directly the valve opening percent of the of the control valves 158, 160 without specifying a set point for the control valves 158, 160. In general, the control system 148 adjusts the flow rates of air and fuel to the burner 130 via the control valves 158, 160 to give TEG bath temperature at set point and give the specified O2 weight-percent in the stack effluent 154.

The lean TEG 112 may discharge from a bottom portion of the reboiler vessel 128 to an accumulator 168 vessel. In lieu of typical piping coupling the reboiler vessel 128 to the accumulator 168, a stripping column 166 (e.g., Stahl column) may be disposed between the reboiler vessel and the accumulator 168. In examples, the stripping column 166 in this illustrated embodiment may be a larger conduit or vessel coupling the reboiler vessel 126 to the accumulator 168. Internals in the stripping column 166 may be packing. The stripping column 166 may be considered as a component of the reboiler vessel 128 or of the accumulator 168. A stripping gas (not shown) may be introduce into the accumulator or into a lower portion of the stripper column 166 to flow upward to strip water from the lean TEG 112 to increase the TEG purity of the lean TEG 112. The stripping gas may include dry nitrogen, natural gas, or fuel gas, and the like.

The accumulator 168 may be labeled as a surge drum. A pump 170 may provide motive force for flow of the lean TEG 112 to the contactor column 102. A level of lean TEG 112 maintained in the accumulator 168 may promote stability of operation of the pump 170. The pump 170 may be a centrifugal pump or a reciprocating pump. In implementations, the pump 170 can be an air-assisted pump.

The lean TEG 112 may be cooled in a heat exchanger 172 (cross-exchanger) with the rich TEG 122 as the cooling medium. Thus, the rich TEG 122 may be heated in the heat exchanger 172 with the lean TEG as the heating medium. The heat exchanger 172 may be a shell-and-tube heat exchanger, a plate-fin heat exchanger, etc.

Prior to the lean TEG 112 entering the contactor column 112, the lean TEG 112 may be cooled in a heat exchanger 174 (cross-exchanger) with the product (dehydrated) natural gas 108 discharging overhead from the contactor column 102 as the cooling medium. The heat exchanger 174 may be a shell-and-tube heat exchanger, a plate-fin heat exchanger, etc.

In certain implementations, the heat exchanger 174 is a jacketed-pipe heat exchanger. For instance, the lean TEG 112 may flow through an inner pipe (conduit) and the natural gas 108 may flow through an outer pipe (conduit) surrounding the inner pipe. Thus, the natural gas 108 may flow in the annulus between the outside diameter of the inner pipe and the inside diameter of the outer pipe.

The control system 148 may facilitate or direct operation of the natural-gas dehydration system 100, such as the supply or discharge of flow streams (including flow rate) and associated control valves, control of operating temperatures and operating pressures, and control of absorption columns, distillation columns, and heat exchangers, and so on. The control system 148 may include a processor 176 and memory 178 storing code (e.g., logic, instructions, etc.) executed by the processor 176 to perform calculations and direct operations of the system 100. The control system 148 may be or include one or more controllers. The processor 176 (hardware processor) may be one or more processors and each processor may have one or more cores. The hardware processor(s) may include a microprocessor, a central processing unit (CPU), a graphic processing unit (GPU), a controller card, circuit board, or other circuitry. The memory 178 may include volatile memory (e.g., cache and random access memory), nonvolatile memory (e.g., hard drive, solid-state drive, and read-only memory), and firmware. The control system 148 may include a desktop computer, laptop computer, computer server, programmable logic controller (PLC), distributed computing system (DSC), controllers, actuators, or control cards. Controllers, including master and slave controllers, may be components of the code stored in the memory 178 and executed by the processor 176. The control system 148 may include control modules and apparatuses distributed in the field.

The control system 152 may receive user input that specifies the set points of control devices or other control components in the natural-gas dehydration system 100. The control system 148 typically includes a user interface for a human to enter set points and other targets or constraints to the control system 148. In some implementations, the control system 152 may calculate or otherwise determine set points of control devices. The control system 148 may be communicatively coupled to a remote computing system that performs calculations and provides direction including values for set points. In operation, the control system 148 may facilitate processes of the system 100 including to direct operation of the fired-heater reboiler 126, as discussed. Again, the control system 148 may receive user input or computer input that specifies the set points of control components in the system 100. The control system 148 may determine, calculate, and specify the set point of control devices. The determination can be based at least in part on the operating conditions of the system 100 including feedback information from sensors and transmitters, and the like.

Some implementations may include a control room that can be a center of activity, facilitating monitoring and control of the process or facility. The control room may contain a human machine interface (HMI), which is a computer, for example, that runs specialized software to provide a user-interface for the control system. The HMI may vary by vendor and present the user with a graphical version of the remote process. There may be multiple HMI consoles or workstations, with varying degrees of access to data. The control system 148 may also or instead employ local control (e.g., distributed controllers, local control panels, etc.) distributed in the system 100.

An embodiment is a natural-gas dehydration system including a TEG regeneration still column to receive rich TEG, discharge water vapor overhead, and discharge lean TEG from a reboiler vessel for feed to a contactor column. The TEG regeneration system has a fired-heater reboiler including a burner and the reboiler vessel. The system includes an air control valve to control flow rate of air to the burner, and a fuel control valve to control flow rate of fuel (e.g., natural gas) to the burner. The natural-gas dehydration system includes a control system to adjust automatically an air set point of the air control valve and a fuel set point of the fuel control valve to control TEG bath temperature in the reboiler vessel, control weight percent of oxygen gas in stack effluent from the burner, and maintain weight ratio of the air to the fuel at a specified weight ratio. The control system may maintain the weight ratio of the air to the fuel at the specified weight ratio in the control of the TEG bath temperature and in the control of the weight percent of the oxygen gas in the stack effluent.

The natural-gas dehydration system includes a temperature sensor at the reboiler vessel to measure the TEG bath temperature, and a temperature transmitter to indicate the TEG bath temperature as measured by the temperature sensor to the control system. The system may include an oxygen analyzer to measure the weight percent of oxygen gas in the stack effluent, and an instrument transmitter to indicate the weight percent of the oxygen gas as measured by the oxygen analyzer to the control system. The control system may control the TEG bath temperature per a temperature set point and control the weight percent of oxygen gas in the stack effluent to a specified weight-percent range. The control system automatically adjusting the air set point and the fuel set point may be in response to the TEG bath temperature as measured and in response to the weight percent of oxygen gas in the stack effluent as measured. The air set point may be an air flow-rate set point or an air pressure set point. The fuel set point may be a fuel flow-rate set point or a fuel pressure set point.

The natural-gas dehydration system may include an air flow meter to measure the flow rate of the air to the burner, and an instrument transmitter to indicate the flow rate of the air as measure by the air flow meter to the control system. Similarly, the system may include a fuel flow meter to measure the flow rate of the fuel to the burner, and an instrument transmitter to indicate the flow rate of the fuel as measured by the fuel flow meter to the control system.

Figure 2:
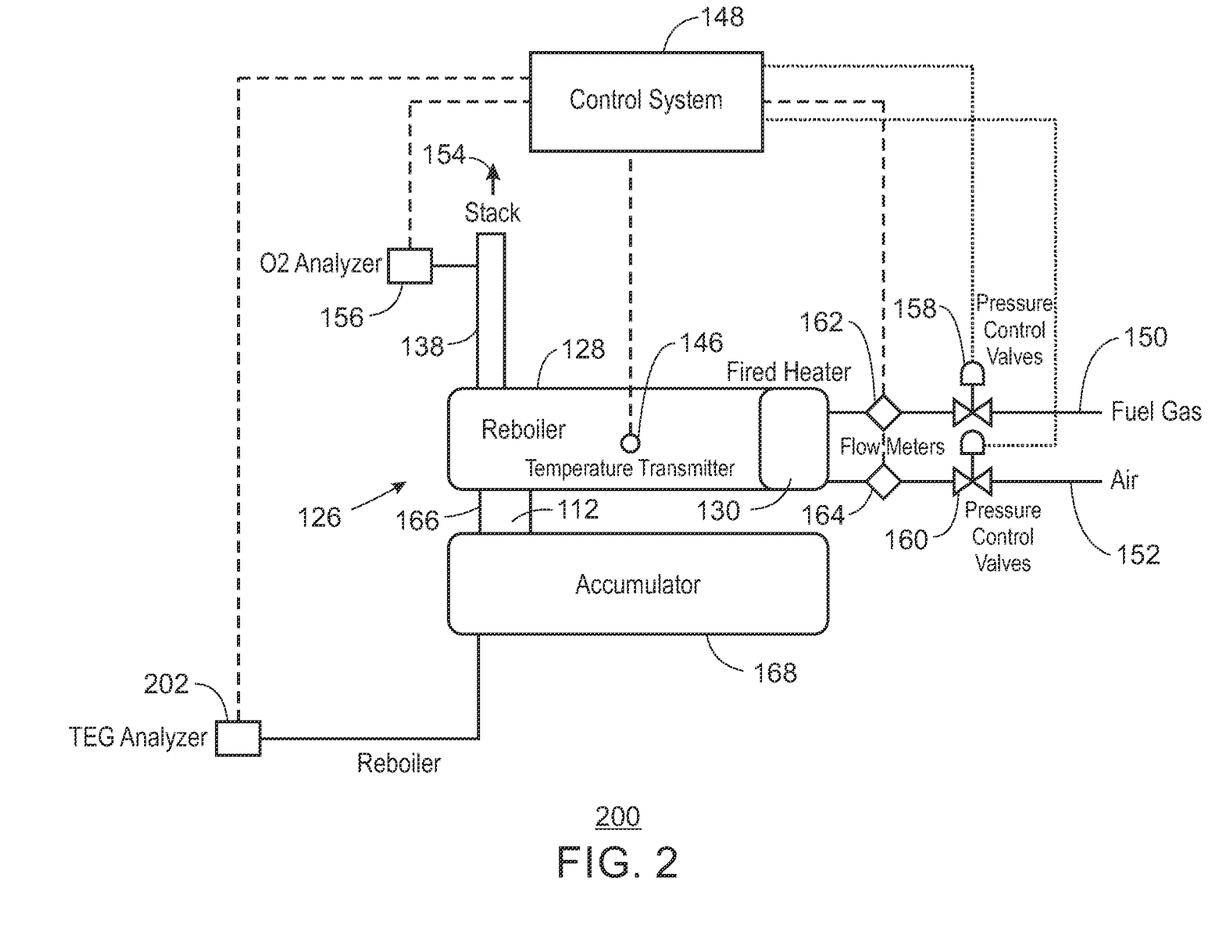
FIG. 2 is a TEG fired-heater reboiler system for TEG regeneration in a natural-gas dehydration system.

FIG. 2 is a TEG fired-heater reboiler system 200 for TEG regeneration in a natural-gas dehydration system, such as the natural-gas dehydration system 100 of FIG. 1. The TEG fired-heater reboiler system 200 includes a fired-heater reboiler 126 that may be analogous or as discussed with respect to FIG. 1. The fired-heater reboiler 126 is coupled to and for the TEG regeneration column still 104 (FIG. 1). As discussed, the fired-heater reboiler 126 in operation heats the TEG bath in the reboiler vessel 128 for the distillation to remove water from the TEG. The combustion of fuel 150 with air 152 in the burner 130 generates the heat. The desired temperature of the TEG bath may be, for example, in the range of 385° F. to 400° F., 390° F. to 400° F., or 390° F. to 395° F.

In operation, a temperature transmitter (TT) may indicate to the control system 148 the TEG bath temperature in the reboiler vessel 128 as measured by a temperature sensor 146 (temperature element or TE). In implementations, the temperature sensor 146 is disposed in the reboiler vessel 126 to be situated in the TEG bath (below the liquid level of the TEG bath) during operation. In some examples, the temperature sensor 146 may be inserted through the wall of the reboiler vessel 126. The temperature transmitter may be positioned at and external to reboiler vessel 128.

The fired-heater reboiler 126 includes the reboiler vessel 128 and the burner 130. The reboiler vessel 128 may be, for example, carbon steel or stainless steel. The selection of the metallurgy or materials of construction for the reboiler vessel 128 may depend, for example, on the impurities in the TEG or water.

The fired burner 130 may be direct or indirect. The example of the burner 130 as depicted in FIG. 1 is an indirect-fired burner. In other implementations, a direct-fired burner may be employed in which the combustion gases directly heat the TEG without a heating element (e.g., without a fire tube).

For a direct-fired burner (e.g., without a fire tube), heat is transferred from the combustion gases to the TEG bath. For instance, there may be a chamber or similar volume, such as of corrugated sheets to separate from direct contact with the heated material or an open flame that is adequately distant to not have direct contact with the heated liquid. For both cases, heating may generally be through radiation as oppose to indirect fired heating which may be through convection.

A user may enter a temperature set point into the control system 148 for the TEG bath temperature. The temperature set point may be in the aforementioned desired ranges for the TEG bath temperature. While typically an individual temperature value (e.g., 393° F., 395° F., etc.) is entered by the user into the control system 148 as the set point, the set point can also be entered as a temperature range (e.g., 393° F. to 395° F.) and thus allowed to float amongst specific values within the range. Such may give more freedom for the control system 148 in the control of the weight percent of O2 in the stack effluent 154 as a secondary variable.

To maintain the TEG bath temperature in the reboiler vessel 128 per the temperature set point of the TEG bath temperature entered by a user, the control system 148 may adjust (e.g., automatically) the fuel set point or valve open percent of the fuel control valve 158 and adjust (e.g., automatically) the air set point or valve open percent of the air control valve 160. The fuel control valve 158 and the air control valve 160 may each may be a pressure control valve or a flow control valve. In controlling the TEG bath temperature (and the O2 weight percent in the stack effluent 154), the control system 144 may maintain constant the weight ratio of air-to-fuel (e.g., 10:1) fed to the burner 130. Thus, a change to the flow rate of the fuel 150 is matched proportionally with a change to the flow rate of the air 152 to keep the air-to-fuel ratio constant. A change to the flow rate of the air 152 is matched proportionally with a change to the flow rate of the fuel 150 to keep the air-to-fuel ratio constant. The constant value for the air-to-fuel ratio may be entered by a user into the control system 148

As mentioned, the control system 148 may control the O2 content in the stack effluent 154 (as measured by the oxygen analyzer 156). The control system 148 may adjust (e.g., automatically) the fuel set point or valve open percent of the fuel control valve 158 and the air set point or valve open percent of the air control valve 160 to maintain the O2 content of the stack effluent 154 in a specified weight-percent range. The specified weight-percent range may be entered by a user into the control system 148. Examples of the specified O2 weight-percent range for the stack effluent 154 include 1 wt % to 4 wt %, 1 wt % to 3 wt %, 2 wt % to 4 wt %, and 2 wt % to 3 wt %. The weight percent of the O2 in the stack effluent 154 as measured by the oxygen analyzer 156 may be indicated to the control system 148 (e.g., in real time).

The oxygen analyzer 156 may be an online analytical instrument that can measure and indicate O2. In some instances, the oxygen analyzer 156 as an online analytical instrument may incorporate a zirconia cell, which includes two electrodes (e.g., precious metal), respectively, on each side of a stabilized zirconia solid electrolyte. The zirconia electrolyte becomes porous to oxygen ions at elevated temperatures, allowing it to operate directly in the stack effluent 154 stream in the stack 138. Thus, such an instrument may avoid having to be an extraction-type measurement device. One side of the measurement cell is exposed to the stack gas 152 containing O2, while the other is placed under the influence of a reference gas, such as plant air or instrument. Any difference between the O2 concentration of the stack effluent 154 gas and the reference gas causes a voltage inversely related to the O2 content of the stack effluent 154 gas.

Lean TEG 112 may discharge from the reboiler vessel 128 through the stripping column 166 to the accumulator 168 vessel. It may be desired that the lean TEG 112 have a purity of at least 99 wt % TEG or a water content of less than 1 wt %.

A TEG analyzer 202 as an online analytical instrument may be disposed to measure the TEG purity of lean TEG 112 or the moisture content (water weight percent) of lean TEG 112. The TEG analyzer 202 may be disposed to analyze the lean TEG in the reboiler vessel 128 (e.g., as overflowed from a weir in the reboiler vessel 128), flowing from the reboiler vessel 128 to the accumulator 168, in the accumulator 168, or flowing from the accumulator 168 toward the contactor column 102 (FIG. 1). The TEG analyzer 202 may be, for example, a spectroscope or spectroscopic analyzer. The TEG purity (or weight percent water) as measured by the TEG analyzer 202 may be indicated or communicated via an instrument transmitter to the control system 148 (e.g., in real time). The instrument transmitter may be a component of the TEG analyzer 202 device.

An example specification for TEG purity of the lean TEG 112 is at least 99 wt %. An example specification for weight percent water in the lean TEG 112 is less than 1 wt %. In response to the TEG purity (or weight percent water) value received at the control system 148 not satisfying specification, a human operator (or the control system 148 automatically) may change the temperature set point of the TEG bath temperature in the reboiler vessel 128. For instance, if the TEG purity is less than the purity specification (e.g., 99 wt %) or the water exceeds the water specification (e.g., 1 wt %), the temperature set point of the TEG bath temperature may be increased.

An embodiment is a method of regenerating TEG in a natural-gas dehydration system, including removing water from TEG in a TEG regeneration still column having a fired-heater reboiler including a burner and a reboiler vessel. The method may include discharging water vapor overhead from the TEG regeneration still column, wherein the water vapor includes the water removed from the TEG. The method may include discharging from a bottom portion of the reboiler vessel the TEG not having the water removed.

The method includes controlling TEG bath temperature in the reboiler vessel and weight percent of oxygen gas in a stack effluent from the burner by a control system automatically adjusting flow of air and fuel to the burner while maintaining a specified weight ratio of the air to the fuel. The fuel may be or include natural gas. The TEG bath temperature may be a primary variable and the weight percent of oxygen gas in the stack effluent may be a secondary variable. The method may include measuring the TEG bath temperature in the reboiler vessel and measuring the weight percent of oxygen in the stack effluent. The method may include indicating the TEG bath temperature as measured to the control system and indicating the weight percent of oxygen in the stack effluent as measured to the control system.

The adjusting flow of the air may involve the control system adjusting, via an air control valve, flow rate of the air to the burner. The adjusting flow of the fuel may involve the control system adjusting, via a fuel control valve, flow rate of the fuel to the burner. The control system adjusting the flow of air and fuel may be in response to the TEG bath temperature as measured. The controlling of the TEG bath temperature may involve the control system maintaining the TEG bath temperature per a set point. The maintaining of the specified weight ratio of the air to the fuel may include the control system automatically adjusting the flow of air and the flow of the fuel proportionally in tandem during the control system controlling the TEG bath temperature and the weight percent of oxygen gas in the stack effluent. The controlling of the weight percent of oxygen gas may include maintaining the weight percent of the oxygen gas in the stack effluent below a specified maximum value or maintaining the weight percent of the oxygen gas in the stack effluent above a specified minimum value, or a combination thereof.

Figure 3:
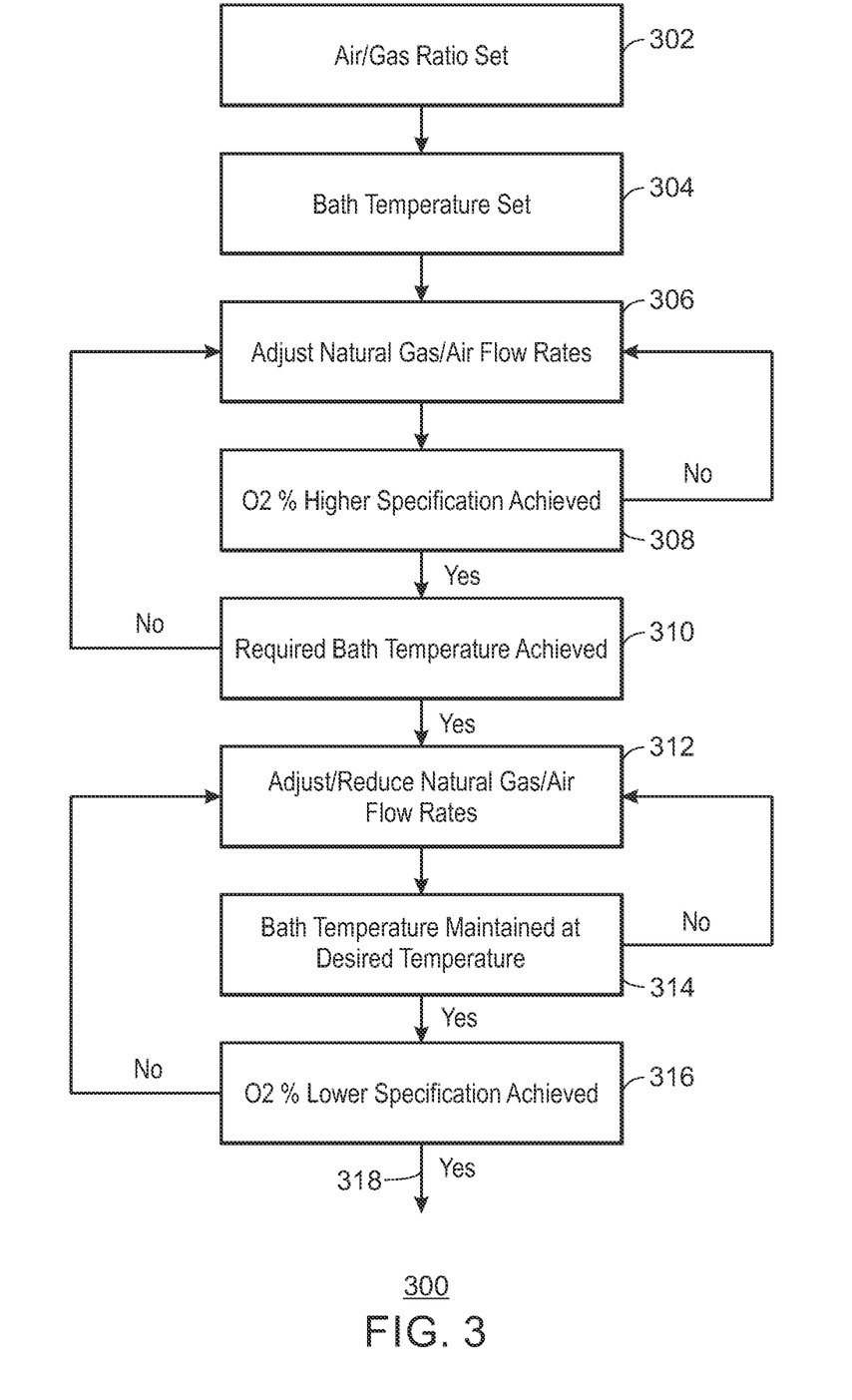
FIG. 3 is a diagram of a workflow for control of a TEG regeneration fired-heater reboiler (of a TEG regeneration column still in a natural-gas dehydration system.

FIG. 3 is a workflow 300 for control of a TEG regeneration fired-heater reboiler (e.g., 126 in FIGS. 1-2) of a TEG regeneration column still in a natural-gas dehydration system. The workflow 300 may be implemented as a control scheme via a control system (e.g., 148 in FIGS. 1-2). The workflow 300 is given as an example. Other workflows applicable to TEG regeneration fired-heater reboiler may combine or otherwise integrate blocks of workflow 300, as well as delete and/or add blocks. The workflow 300 involves control of the supply of fuel and air to the burner of the TEG regeneration fired-heater reboiler. The fuel may be or include natural gas. The air may be, for example, plant air or instrument air at the facility.

At block 302, the air-to-fuel ratio for the burner of the TEG fired-heater reboiler is set. To set the air-to-fuel ratio, a human operator may enter the desired (specified) numerical value for the ratio into the control system. During operation of the TEG fired-heater reboiler (including through workflow 300), the air-to-fuel ratio may be generally maintained constant by the control system at the entered specified value. The ratio may be a mass ratio. An example numerical for the ratio as a mass (weight) ratio is 10:1. A new value for the air-to-fuel ratio may be specified and entered, for example, in response to changes in the quality or composition of the fuel.

At block 304, the TEG bath temperature in the TEG fired-heater reboiler is set. This may involve a human operator entering a temperature set point for the TEG bath temperature into the control system. The numerical value for the temperature set point entered may be in response to the TEG bath temperature adequate to drive the distillation including for vaporization of water from the TEG in the reboiler vessel. The temperature set point may be, for example, in the range of 390° F. to 400° F. (or 390° F. to 395° F.). The TEG bath temperature should generally be maintained below the degradation temperature (404° F.) of the TEG. For determination of the temperature set point to specify in view of the degradation temperature, a margin (e.g., at least 4° F., 5° F., 8° F., 9° F., etc.) below the TEG degradation temperature may considered to account for occasional process instability or upset.

At block 306, the air flow rate and the fuel flow rate to the burner are adjusted (e.g., via control valves) by the control system to meet the temperature set point of the TEG bath temperature and for the O2 content in the burner stack effluent to below a higher (upper) specification. The adjustments to the flow rates of the air and fuel may be proportional and in tandem to maintain the air-to-fuel ratio set in block 302. For instance, if the fuel flow rate is increased, the air flow rate is increased proportionally. If the fuel flow rate is decreased, the air flow rate is decreased proportionally. If the air flow rate is increased, the fuel flow rate is increased proportionally. If the air flow rate is decreased, the fuel flow rate is decreased proportionally. Generally, as mentioned, the adjustments of the air and fuel are made in tandem. The combined amount of flow of air and fuel is increased or decreased.

At decision block 308, the control system determines if the O2 content (e.g., units of wt %) in the burner stack effluent achieves or satisfies (meets) the higher specification, which may be an upper limit (e.g., 3 wt % or 4 wt %). The control system compares the O2 reading from the oxygen analyzer on the stack effluent with the higher specification. To achieve or satisfy the higher specification means that the O2 content is less than the higher specification. The higher specification may have been entered into the control system, for example, by a human operator.

It may be desired to maintain the weight percent of O2 in the stack effluent below a maximum value (the higher or upper specification). The O2 weight percent exceeding the maximum value may be indicative of incomplete combustion at the burner and that fuel is being wasted. A benefit to maintaining the O2 weight percent in the stack effluent below the specified maximum value may be that less greenhouse gases (e.g., CO2) are discharged in the stack effluent to the environment.

If the answer at decision block 308 is "no" (e.g., the control system determines that the O2 content in the stack effluent exceeds the higher specification), the workflow returns to block 306. At block 306, the control system may further adjust (e.g., decrease) the air and fuel rates to the burner to reduce the O2 weight percent in the stack effluent to below the higher specification. The air-to-fuel ratio set in block 302 is maintained. If the answer at decision block 308 is "yes" (e.g., the control system determines that the O2 content in the stack effluent does not exceed the higher specification), the workflow continues to decision block 310.

At decision block 310, if the TEG bath temperature (e.g., as measured by a temperature sensor at the reboiler vessel) does not match the desired bath temperature set in block 304 (e.g., the measured bath temperature does not meet the set point of the bath temperature), then the workflow returns to block 306. At block 306, the control system makes further adjustments to the air and fuel rates to the burner so that the measured bath temperature agrees with the set bath temperature (block 304). The flow rates of air and fuel are adjusted to give the TEG bath temperature at the temperature set point entered in block 304.

The air flow rate and the fuel flow rate are adjusted (e.g., via control valves) by the control system to meet the temperature set point of the TEG bath temperature. The combined amount of air and fuel may generally be increased (to increase TEG bath temperature) in response to the TEG bath temperature falling below the temperature set point. The combined amount of air and fuel may generally be decreased (to decrease TEG bath temperature) in response to the TEG bath temperature exceeding (going above) the temperature set point. The air-to-fuel ratio set in block 302 is maintained. At decision block 310, if the measured TEG bath temperature matches the desired bath temperature set in block 304 (e.g., the measured TEG bath temperature matches the temperature set point), the workflow continues to block 312.

At block 312, the control system adjusts (as needed) the flow rates of air and fuel (e.g., via the air and fuel control valves, respectively) to maintain the TEG bath temperature at the temperature set point entered in block 304. In implementations, the flow rates of air and fuel can be further slightly reduced to decrease the O2 content in the stack effluent towards a lower specification of the measure O2 is at or near the higher specification. The air-to-fuel ratio set in block 302 is maintained.

As for comparison of block 306 to block 312, block 306 may be responsible to meet the desired bath temperature prior to checking the O2 content. For block 312 after the desired bath temperature is achieved, the system via the O2 analyzer may evaluate if the O2 is at its upper limit (or beyond) to determine room for adjustments downward and then adjusts accordingly to reduce O2 toward or to the lower limit (which may be a desirable point with more efficiency). The "Reduce" in block 312 may allude to if both the bath temperature and O2 ranges are achieved, the system may adjust the fuel and air flows to reduce the O2 levels to the lower limit, thus reducing the fuel gas consumed)

At decision block 314, if the bath temperature is not maintained at the desired temperature, the workflow returns to block 312. At decision block 314, if the bath temperature is maintained at the desired temperature, the workflow continues to decision block 316.

At decision block 316, if the O2 weight percent in the stack effluent is below a lower specification (lower limit), the workflow returns to block 312. At block 312, the control system may increase the flow rates of air and fuel in combination to raise the O2 weight percent in the stack effluent to above the lower specification (e.g., 1 wt % or 2 wt %). The air-to-fuel ratio set in block 302 is maintained. It may be desired to maintain the weight percent of O2 in the stack effluent 154 above a minimum value so to promote or reflect that an adequate amount (or beneficial amount) of combustion occurs at the burner 130 for heating the TEG bath. At decision block 316, if the O2 weight percent in the stack effluent is above the lower specification, the workflow 300 continues as indicated by reference numeral 318 to enact the foregoing workflow 300 adjustments as needed to control the TEG bath temperature and the O2 content in the stack effluent.

The TEG bath temperature may be a primary variable and the O2 content in the stack effluent is secondary to (lower priority than) than the TEG bath temperature. The O2 weight percent in the stack effluent may be allowed to exceed the higher specification (or fall under the lower specification) if needed to maintain the TEG bath temperature at the temperature set point. In implementations, the adjustments to fuel and air rates may be satisfactorily gross adjustments for the TEG bath temperature with the adjustments to fuel and air rates for the O2 content in the stack effluent as fine tuning such that both variables of TEG bath temperature in the reboiler vessel and O2 content in the stack effluent can be satisfied.

Figure 4:
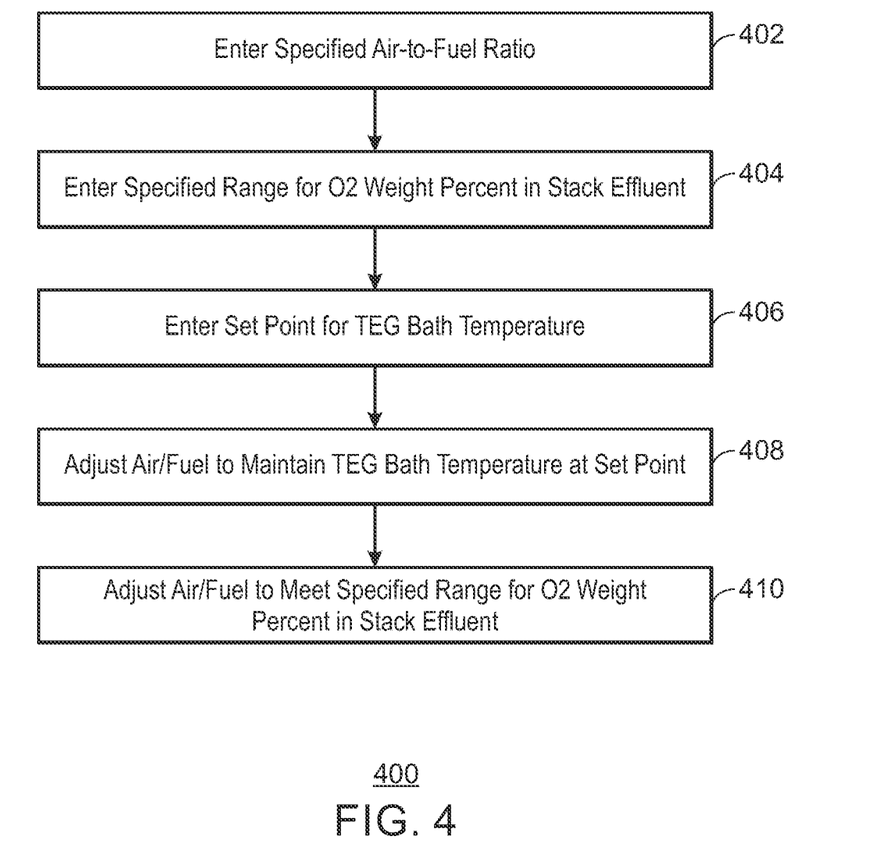
FIG. 4 is a diagram of a workflow for control of a TEG regeneration fired-heater reboiler (of a TEG regeneration column still in a natural-gas dehydration system.

FIG. 4 is a workflow 400 for control of a TEG regeneration fired-heater reboiler (e.g., 126 in FIGS. 1-2) of a TEG regeneration column still in a natural-gas dehydration system. The workflow 400 may be implemented as a control scheme via a control system (e.g., 148 in FIGS. 1-2). As discussed with respect to preceding figures, the TEG regeneration fired-heater reboiler includes a burner and a reboiler vessel.

At block 402, the air-to-fuel mass ratio specified for the burner of the TEG fired-heater reboiler is entered into the control system. This air-to-fuel ratio may be generally maintained constant by the control system at the entered specified value.

At block 404, the specified range (e.g., 1 wt % to 4 wt %, or 2 wt % to 3 wt %) for O2 weight percent in the stack effluent is entered into the control system. The specified range has a lower threshold or limit (e.g., 1 wt % or 2 wt %) and an upper threshold or limit (e.g., 3 wt % or 4 wt %).

At block 406, a temperature set point (e.g., in the range of 390° F. to 395° F.) for the TEG bath temperature in the reboiler vessel of the TEG fired-heater reboiler is entered into the control system. The TEG bath temperature should generally be maintained below 404° F., which is the degradation temperature of TEG.

At block 408, the air flow rate and the fuel flow rate to the burner are adjusted via control valves by the control system to meet and maintain the temperature set point of the TEG bath temperature entered in block 406. The control system may compare the actual bath temperature as measured by a temperature sensor to the temperature set point to determine the adjustments in flow rates. The adjustments to the flow rates of the air and fuel may be proportional to each other to maintain the air-to-fuel ratio entered in block 402. If the measured TEG bath temperature is below the temperature set point, the adjustments may increase the flow rates of the air and fuel in tandem to increase the TEG bath temperature to meet the temperature set point. If the measured TEG bath temperature is higher than temperature set point, the adjustments may decrease the flow rates of the air and fuel in tandem to decrease the TEG bath temperature to meet the temperature set point.

At block 410, the air flow rate and the fuel flow rate to the burner are adjusted via the control valves by the control system to satisfy and maintain the specified range of the O2 weight percent for the stack effluent entered in block 406. The control system maintains the O2 weight percent above the lower limit and below the upper limit. However, the control system will generally not implement adjustments that cause the TEG bath temperature to deviate from the temperature set point entered in block 406. Further, the air-to-fuel ratio entered in block 402 is maintained.

Figure 5:
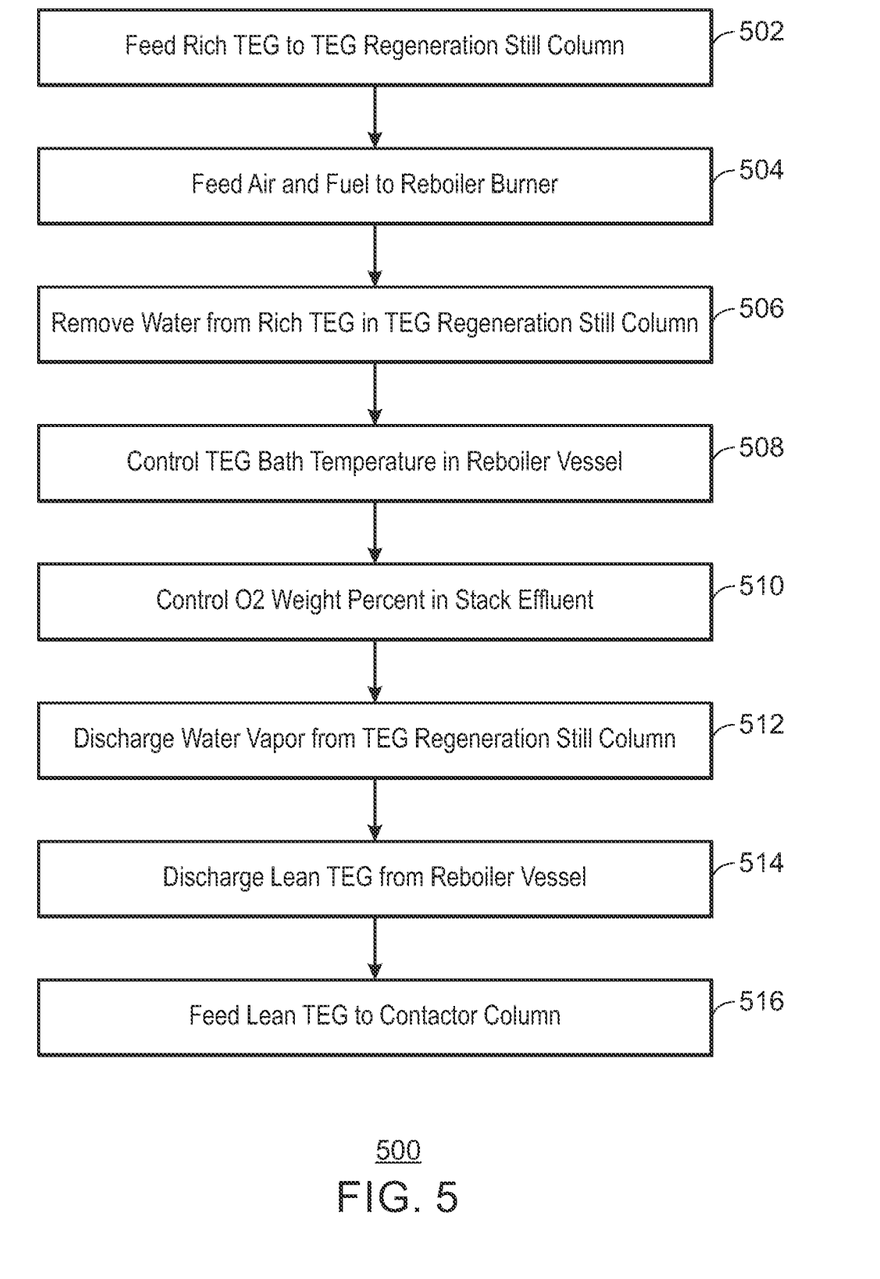
FIG. 5 is a method of regenerating TEG in a natural-gas dehydration system.

FIG. 5 is a method 500 of regenerating TEG in a natural-gas dehydration system. An example of a natural-gas dehydration system is given in FIG. 1.

At block 502, the method includes feeding rich TEG to a TEG regeneration still column having a fired-heater reboiler including a burner and a reboiler vessel. The rich TEG may be introduced to the column vessel. As discussed, the rich TEG is TEG rich in water. The rich TEG may have a concentration of water of at least 2 wt %, at least 3 wt %, at least 4 wt %, at least 5 wt %, or at least 6 wt %.

At block 504, the method includes feeding air and fuel to the burner at a specified weight ratio of the air to the fuel. In one example, the specified weight ratio is at least 10. In implementations of method 500, a control system in controlling the TEG bath temperature in the reboiler vessel and the weight percent of oxygen gas in the stack effluent, as presented in subsequent blocks below, may involve the control system not deviating from the specified weight ratio of the air to the fuel fed to the burner.

At block 506, the method includes removing water from the rich TEG in the TEG regeneration still column. The TEG regeneration still column as a distillation column may remove the water from the rich TEG via distillation. The TEG regeneration still column may remove the water by vaporizing water from the TEG in the reboiler vessel. The TEG regeneration still column may remove the water via packing or trays in the column vessel providing for distillation stages.

At block 508, the method includes controlling TEG bath temperature in the reboiler vessel per a temperature set point automatically via the control system. The controlling of the TEG bath temperature may involve the control system adjusting, via an air control valve, flow rate of the air to the burner and adjusting, via a fuel control valve, flow rate of the fuel to the burner. The air-to-fuel ratio of the air and fuel fed to the burner is generally maintained.

At block 510, the method includes controlling automatically via a control system the weight percent of oxygen gas in a stack effluent from the burner. The controlling of the weight percent of oxygen gas in the stack effluent in the specified range may involve the control system adjusting, via the air control valve, the flow rate of the air to the burner and adjusting, via the fuel control valve, the flow rate of the fuel to the burner. The controlling (block 508) of the TEG bath temperature and the controlling of the weight percent of oxygen gas in the stack effluent involve the control system automatically adjusting flow of the air and the fuel to the burner at the specified weight ratio of air to fuel. In other words, the air-to-fuel mass ratio of the air and fuel fed to the burner is generally maintained.

At block 512, the method may include discharging water vapor overhead from TEG regeneration still column. The water vapor includes the water removed (distilled) from the rich TEG. In some embodiments, the water vapor may be cooled via a heat exchanger (e.g., piping coils) in an upper portion of the TEG regeneration still column before the water discharges from the top part of the TEG regeneration still column. In examples, the cooling medium flowing through the piping coils is rich TEG before introduced into the TEG regeneration still column as feed for distillation (water removal).

At block 514, the method may include discharging lean TEG from a bottom portion of the reboiler vessel. As discussed, the lean TEG is TEG lean in water. The lean TEG has less water than the rich TEG. The lean TEG may generally be the rich TEG that entered the TEG distillation still column minus the water removed from the rich TEG 112 by the TEG distillation still column. The lean TEG 112 may have a concentration of water less than 2 wt %, less than 1.5 wt %, less than 1 wt %, or less than 0.5 wt %. The lean TEG may have a TEG purity (concentration of TEG) of at least 98 wt %, at least 98.5 wt %, at least 99 wt %, or at least 99.5 wt %.

At block 516, the method may include feeding the lean TEG to a contactor column to absorb water from natural gas in the contactor column to dehydrate the natural gas. The lean TEG may flow through an accumulator vessel or surge drum. The lean TEG may be cooled in route to the contactor column, such as in one or more heat exchangers. For instance, the lean TEG may be cross-exchanged with rich TEG from the contactor column as a cooling medium. In implementations, the lean TEG may also be cross-exchanger with dehydrated natural gas from the contactor column as a cooling medium. The lean TEG (which enters the top portion of the contactor column) may be cooled, for example, to 8° F. to °15 F. above the inlet temperature of wet natural gas that enters the bottom portion of the contactor column. Such may be beneficial because equilibrium between the TEG and the water vapor in the natural gas is affected by temperature.

A number of implementations have been described. Nevertheless, it will be understood that various modifications may be made without departing from the spirit and scope of the disclosure.

What is claimed is:

1. A method of regenerating triethylene glycol (TEG) in a natural-gas dehydration system, comprising:
    removing water from TEG in a TEG regeneration still column having a fired-heater reboiler comprising a burner and a reboiler vessel;
    controlling TEG bath temperature in the reboiler vessel and weight percent of oxygen gas in a stack effluent from the burner by a control system comprises automatically adjusting flow rate of the air via an air control valve disposed along an air conduit conveying the air from a supply header to the air control valve and from the air control valve to the burner, and adjusting flow rate of the fuel via a fuel control valve disposed along a conduit conveying the fuel to the burner while maintaining a specified weight ratio of the air to the fuel, wherein the air flows through the air control valve, and wherein the air does not comprise ambient air;
    measuring the flow rate of the air via an air flow meter disposed along the air conduit conveying the air to the burner;
    measuring, via an oxygen analyzer disposed along a stack having the stack effluent, the weight percent of oxygen gas in the stack effluent; and
    indicating the weight percent of oxygen gas as measured to the control system, wherein controlling the weight percent of oxygen gas by the control system automatically adjusting the flow rate of the air and the flow rate of the fuel is in response to the weight percent of oxygen gas as measured.

2. The method of claim 1, wherein the fuel comprises natural gas.

3. The method of claim 1, comprising:
    providing the TEG from a contactor column of the natural-gas dehydration system to the TEG regeneration still column; and
    measuring the TEG bath temperature in the reboiler vessel, wherein adjusting the flow rate of the fuel via the fuel control valve comprises altering a set point of the fuel control valve.

4. The method of claim 3, comprising indicating the TEG bath temperature as measured to the control system, wherein providing the TEG comprises:
    discharging rich TEG from a bottom portion of the contactor column to a flash vessel;
    removing hydrocarbons from the rich TEG in the flash vessel; and
    discharging the rich TEG from the flash vessel to the TEG regeneration still column without the hydrocarbons removed in the flash vessel.

5. The method of claim 1, wherein the TEG bath temperature is a primary variable and the weight percent of oxygen gas in the stack effluent is a secondary variable.

6. The method of claim 1, comprising measuring the flow rate of the fuel via a fuel flow meter disposed along the conduit conveying the fuel to the burner, wherein the oxygen analyzer comprises an online analytical instrument.

7. The method of claim 1, comprising measuring the TEG bath temperature in the reboiler vessel and indicating the TEG bath temperature as measured to the control system, wherein the control system adjusts the flow rate of the air and the flow rate of the fuel in response to the TEG bath temperature as measured, and wherein controlling the TEG bath temperature comprises the control system maintaining the TEG bath temperature per a set point.

8. The method of claim 1, wherein maintaining the specified weight ratio of the air to the fuel comprises the control system automatically adjusting the flow rate of air and the flow rate of the fuel proportionally in tandem during the control system controlling the TEG bath temperature in the reboiler vessel and during controlling the weight percent of oxygen gas in the stack effluent.

9. The method of claim 1, wherein controlling the weight percent of oxygen gas comprises maintaining the weight percent of the oxygen gas in the stack effluent below a specified maximum value or maintaining the weight percent of the oxygen gas in the stack effluent above a specified minimum value, or a combination thereof.

10. The method of claim 1, comprising discharging water vapor overhead from the TEG regeneration still column, wherein the water vapor comprises the water removed from the TEG.

11. The method of claim 1, comprising discharging the TEG not having the water removed from a bottom portion of the reboiler vessel.

12. A method of regenerating triethylene glycol (TEG) in a natural-gas dehydration system, comprising:
feeding rich TEG to a TEG regeneration still column having a fired-heater reboiler comprising a burner and a reboiler vessel, wherein the rich TEG comprises TEG rich in water;
feeding air via an air control valve to the burner and fuel via a fuel control valve to the burner at a specified weight ratio of the air to the fuel, wherein the air control valve is disposed along an air conduit conveying the air from a supply header to and through the air control valve to the burner, wherein the air does not comprise ambient air, and wherein the fuel control valve is disposed along a conduit conveying the fuel to the burner;
measuring flow rate of the air via an air flow meter disposed along the air conduit conveying the air to the burner;
controlling TEG bath temperature in the reboiler vessel per a set point automatically via a control system;
controlling weight percent of oxygen gas in a stack effluent from the burner in a specified weight-percent range automatically via the control system;
removing water from the rich TEG in the TEG regeneration still column, wherein controlling the TEG bath temperature and controlling the weight percent of oxygen gas in the stack effluent comprise the control system automatically adjusting flow of the air via the air control valve to the burner and flow of the fuel via the fuel control valve to the burner at the specified weight ratio;
measuring, via an oxygen analyzer disposed along a stack having the stack effluent, the weight percent of oxygen gas in the stack effluent; and
indicating the weight percent of oxygen gas as measured to the control system, wherein controlling the weight percent of oxygen gas by the control system automatically adjusting the flow of the air and the flow of the fuel is in response to the weight percent of oxygen gas as measured, and wherein feeding the air and the fuel to the burner at the specified weight ratio comprises the control system not deviating from the specified weight ratio during the controlling of the TEG bath temperature in the reboiler vessel and the controlling of the weight percent of oxygen gas in the stack effluent.

13. The method of claim 12, wherein controlling the TEG bath temperature comprises the control system adjusting, via the air control valve, the flow of the air comprising the flow rate of the air to the burner and adjusting, via the fuel control valve, the flow of the fuel comprising flow rate of the fuel to the burner, wherein the oxygen analyzer comprises an online analytical instrument.

14. The method of claim 13, comprising measuring the flow rate of the fuel via a fuel flow meter disposed along the conduit conveying the fuel to the burner, wherein controlling the weight percent of oxygen gas in the stack effluent to the specified weight-percent range comprises the control system adjusting, via the air control valve, the flow rate of the air to the burner in response to the weight percent of oxygen gas as measured.

15. The method of claim 12, comprising discharging water vapor overhead from TEG regeneration still column, wherein the water vapor comprises the water removed from the rich TEG, and wherein the oxygen analyzer comprises an online analytical instrument.

16. The method of claim 12, comprising discharging lean TEG from a bottom portion of the reboiler vessel, wherein the lean TEG is TEG lean in water, wherein the lean TEG comprises less water than the rich TEG.

17. The method of claim 16, comprising feeding the lean TEG to a contactor column to absorb water from natural gas in the contactor column, wherein the rich TEG comprises a concentration of water of at least 2 weight percent, and wherein the lean TEG comprises a concentration of water of less than 1.5 weight percent.

18. The method of claim 17, wherein feeding rich TEG to the TEG regeneration still column comprises:
discharging rich TEG from a bottom portion of the contactor column to a flash vessel;
removing hydrocarbons from the rich TEG in the flash vessel; and
discharging the rich TEG from the flash vessel to the TEG regeneration still column without the hydrocarbons removed in the flash vessel.

* * * * *